(12) United States Patent
Ma

(10) Patent No.: US 7,588,938 B2
(45) Date of Patent: Sep. 15, 2009

(54) NEURAL STEM CELL-COLLAGEN-BIOREACTOR SYSTEM TO CONSTRUCT A FUNCTIONAL EMBRYONIC BRAIN-LIKE TISSUE

(75) Inventor: Wu Ma, Silver Spring, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 797 days.

(21) Appl. No.: 10/911,766

(22) Filed: Aug. 4, 2004

(65) Prior Publication Data

US 2006/0030043 A1 Feb. 9, 2006

(51) Int. Cl.
C12N 5/02 (2006.01)
C12N 5/08 (2006.01)
C12N 5/06 (2006.01)

(52) U.S. Cl. .................. 435/394; 435/368; 435/353

(58) Field of Classification Search .............. None
See application file for complete search history.

(56) References Cited

U.S. PATENT DOCUMENTS

2002/0177224 A1* 11/2002 Madry et al. ............... 435/325

OTHER PUBLICATIONS

Freed Le, Vunjak-Novakovic G, Microgravity tissue engineering, 1997, In vitro Cell Dev Biol-Animal 33: 381-385.*
Low HP, Savarese TM, Schwartz WJ, Neural precursor cells from rudimentary tissue-like structures in a rotating-wall vessel bioreactor, 2001, In vitro Cell Dev Bio-Animal 37: 141-147.*
Alberts B, Bray D, Lewis J, Raff M, Roberts K, Watson JD, Molecular Biology of the Cell, Third Edition, Garland Publishing, New York 1994, pp. 995-1000.*
Carrier RL, Papadaki M, Rupnick M, Schoen FJ, Bursac N, Langer R, Freed LE, Vunjak-Novakovic G, Cardiac tissue engineering: cell seeding, cultivation parameters, and tissue construct characterization, 1999, Biotechnol Bioeng 64: 580-589.*
Carpenter MK, Cui X, Hu Z-y, Jackson J, Sherman S, Seiger A, Wahlberg LU, In Vitro expansion of a multipotent polulation of human neural progenitor cells, 1999, Exp Neurol 158: 265-278.*
Schmidt CE, Leach JB, Neural tissue engineering: strategies for repair and regeneration, 2003, Annu Rev Biomed Eng 5: 293-347.*
Freed, L.E. et al., "Chondrogenesis in a Cell-Polymer-Bioreactor System", 1998, Exp. Cell Res., vol. 240: pp. 58-65.*
De Bari, C. et al., "Multipotent Mesenchymal Stem Cells From Adult Human Synovial Membrane", 2001, Arthrit. Rheum., vol. 44: pp. 1928-1942.*
Young, H. et al., "Human Reserve Pluripotent Mesenchymal Stem Cells Are Present in the Connective Tissues of Skeletal Muscle and Dermis Derived From Fetal, Adult, and Geriatric Donors", 2001, Anat. Record, vol. 264: pp. 51-62.*
Vunjak-Novakovic, G. et al., "Microigravity Studies of Cells and Tissues", 2002, Ann N.Y. Acad. Sci., vol. 974: pp. 504-517.*
Carrier et al, "Cardiac tissue engineering cell seeding, cultivation parameters and tissue construct characterization.", Biotechnology and Bioengineering, vol. 64, No. 5, pp. 580-589, 1999.
Freed et al, "Tissue engineering of cartilage in space", Proc. Natl. Acad. Sci., vol. 94, pp. 13885-13890, 1997.
Freed et al, "Cultivation of Cell-Polymer Tissue Constructs in Simulated Microgravity", Biotechnology and Bioengineering, vol. 46, pp. 306-313, 1995.
Goodwin et al, "Rotating-Wall Vessel Coculture of Small Intestine as a Prelude to Tissue Modeling: Aspects of Simulated Microgravity", Society for Experimental Biology and Medicine, vol. 202, pp. 181-192, 1993.
Griffith et al, "Tissue Engineering-Current Challenges and Expanding Opportunities", Science Magazine, vol. 295, pp. 1009-1014, 2002.
Jessup et al, "Prospects for Use of Microgravity-Based Bioreactors to Study Three-Dimensional Host-Tumor Interactions in Human Neoplasia", Journal of Cellular Biochemistry, vol. 51, pp. 290-300, 1993.
Margolis et al, "Long Term Organ Culture of Human Prostate Tissue in a NASA-Designed Rotating Wall Bioreactor", The Journal of Urology, vol. 161, pp. 290-297, 1999.
O'Connor et al, "Primary Neural Precursor Cell Expansion, Differentiation and Cytosolic Ca2+ Response in Three-Dimensional Collagen Gel", Journal of Neuroscience Methods, vol. 102, pp. 187-195, 2000.
Unsworth et al, "Tissue Assembly in Microgravity", Principles of Tissue Engineering, 2nd. Edt., pp. 157-164, 2000.
Unsworth et al, "Growing Tissue in Microgravity", Nature Medicine, vol. 4, No. 8, pp. 903-907, 1998.
Zhang et al., "Self-Renewing Canine Oligodendroglial Progenitor Expanded as Oligospheres" *J. Neuroscience Res.*, 54:181-190 (1998).

* cited by examiner

*Primary Examiner*—Michael Burkhart
(74) *Attorney, Agent, or Firm*—John K. Karasek; Joseph T. Grunkemeyer

(57) ABSTRACT

A method of generating tissue from stem and progenitor cells is disclosed. Primary mammalian stem cells and progenitor cells are placed in an extracellular matrix. The matrix is maintained in a culture medium and a microgravity environment.

6 Claims, 5 Drawing Sheets

NEURAL STEM CELL-COLLAGEN-BIOREACTOR SYSTEM TO CONSTRUCT A FUNCTIONAL EMBRYONIC BRAIN-LIKE TISSUE

BACKGROUND OF THE INVENTION

1. Field of the Invention

The invention relates generally to methods of culturing stem cells and progenitor cells.

2. Description of the Prior Art

Functional recovery following brain and spinal cord injuries and neurodegenerative diseases is likely to require the transplantation of exogenous neural cells and tissues, since the mammalian central nervous system (CNS) has little capacity for self-repair. However, neural cell or tissue transplantation is limited by the lack of tissue donors and the low survival rate of grafted cells. There is a need for an alternative strategy for building biological substitutes, such as a three-dimensional (3D) culture of neural cells to repair or replace the function of damaged nerve tissues. Tissue engineering that combines neural cells and polymer scaffolds may generate functional 3D constructs to serve as replacement tissues or organs (Bellamkonda, 1998; Woerly, 1999). Since neurons are not capable of proliferating and neurons in culture are short-lived, there remain significant challenges for neural tissue engineering. Recent advances in neural stem/progenitor cell biology show that progenitors can be isolated from the embryonic or adult CNS and placed in culture, where they are highly proliferative and differentiate into neurons and glial phenotypes (McKay, 1997; Ma, 1998; 2000; Gage, 1998; 2000; Maric, 2000; 2003). Therefore, CNS stem and progenitor cells have the potential to be a valuable source of specific neural cell types, which could be used for the neural tissue engineering (Gage, 1995; Fisher, 1997).

Polymer scaffolds play a critical role in neural tissue engineering, since neural progenitors and progeny like most other mammalian cells are anchorage-dependent and require the attachment to a solid surface (Ruoslahti, 1997). Among polymer scaffolds, hydrogels are attractive because of their highly porous and hydrated structure that allow cells to assemble spontaneously and become organized into a recognized tissue and permit the infusion of nutrients and oxygen into, and exit of waste products and $CO_2$ out of the cells. Collagen is a biologically derived hydrogel, the major class of insoluble fibrous protein in the extracellular matrix (ECM). Neural progenitor cells isolated from embryonic rat CNS tissue rapidly proliferate and differentiate into neurons and astrocytes in type I collagen gels (O'Conner, 2000). In response to collagen and basic fibroblast growth factor (bFGF), the collagen-entrapped neural progenitor cells rapidly expand and differentiate spontaneously into excitable neurons and formed synapses (Ma, 2004). The collagen demonstrates a critical support for neuronal survival and synaptic activity (O'Conner, 2001; O'Shaughnessy, 2003). Such stem/progenitor cell-collagen constructs may be particularly useful as engineered neural tissue replacement for brain or spinal cord injury.

However, neural tissue engineering using the cell-collagen constructs remains a significant challenge. The cells in the constructs are typically short-lived due to the difficulty in exchanging oxygen and nutrients, which compromises cells and leads to cell death. Cell culture in a simulated microgravity environment offers two beneficial factors: low fluid shear stress, which promotes cell-cell contacts, and initiation of differentiating cellular signaling (Goodwin, 1993); and randomized gravitational vectors, which affect intracellular signal transduction and gene expression (Jessup, 1993). The aggregation-differentiation-promoting effects of the RWV culture conditions provide an excellent in vitro system to further differentiate bioengineered tissue-equivalents, such as skin (for review see Unsworth, 2000), cartilage (Freed, 1997), cardiac cells (Carrier, 1999), prostate (Margolis, 1999), kidney and liver fragments (for review see Unsworth, 2000). A rotating wall vessel (RWV) bioreactor was also used to form a rudimentary tissue-like structure from neural precursor cells (Low, 2001).

SUMMARY OF THE INVENTION

The invention comprises a method of growing tissue comprising the steps of providing primary mammalian stem cells and progenitor cells, placing the stem cells and the progenitor cells in an extracellular matrix, and maintaining the matrix in a culture medium and a microgravity environment.

BRIEF DESCRIPTION OF THE DRAWINGS

A more complete appreciation of the invention will be readily obtained by reference to the following Description of the Example Embodiments and the accompanying drawings.

DETAILED DESCRIPTION OF THE EXAMPLE EMBODIMENTS

Figure 1:
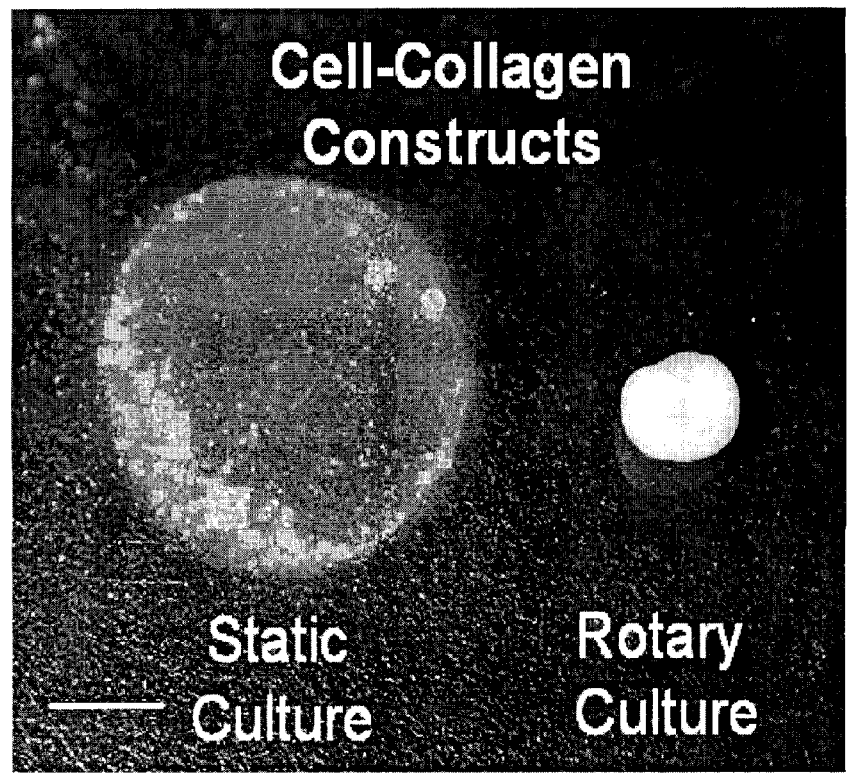
FIG. 1 shows a cell-collagen construct cultured in a RWV bioreactor.

A methodology called "stem cell-collagen-bioreactor system" described herein can enable the engineering of living tissue in vitro. The strategy can provide a combination of naturally derived polymer scaffolds, simulated microgravity, and soluble factors that supply the physical and chemical cues to guide proliferation and differentiation of stem and progenitor cells isolated from the embryonic mammal, including, but not limited to, neural stem and progenitor cells from an embryonic brain. The strategy can be used to achieve an engineered living tissue construct with unique embryonic brain architecture generated by using the system. In the engineered construct, neural stem and progenitor cells can actively proliferate, differentiate into neurons, astrocytes, and oligodendrocytes, and form a complex three-layered architecture that emulates the cerebral cortex of an embryonic brain. The engineered embryonic brain-like tissues have potential use in tissue replacement therapy for injured brain and spinal cord and neurodegenerative diseases, as well as in serving as tissue surrogate for drug screening and detection of environmental toxins.

In order to assemble single cells into highly organized, functional nerve tissue without restricted diffusion of oxygen and nutrients, simulated microgravity created by NASA-designed RWV bioreactors has been used. Neural stem and progenitor cells immobilized in collagen gels can be cultured in vitro in a RWV bioreactor for up to 10 weeks. The collagen-entrapped cells both proliferate and differentiate, and form multi-layered tissues that resemble developing neural tissue.

The strategy and results described below involves entrapment of neural stem and progenitor cells into a collagen gel, which is then maintained for weeks in a RWV bioreactor. The in vitro system includes three components. The first component is primary mammalian stem and progenitor cells including, but not limited to, neural stem and progenitor cells. Such cells may be from any mammal, including, but are not limited to, rat or human, and may be isolated from the embryonic cortical neuroepithelium at the beginning of neurogenesis. The cells may be at least 95% proliferative. The second component is an extracellular matrix, such as type I collagen, fibronectin, or laminin, as the ECM protein to promote cell attachment, survival, growth and differentiation in three dimensions. A culture medium is also in the ECM. The third component is a microgravity environment, such as a NASA-designed RWV bioreactor that rotates around its central spin axis at a speed of 10-15 rpm, so as to maintain the forming tissue in a state of continuous free-fall. This state offers a potentially optimized microgravity environment to regulate tissue development. The RWV is described at Freed and Vunjak-Novakovic, 1995).

There can be at least three advantages to this strategy for neural tissue engineering. First, the use of neural stem and progenitor cells, which are capable of both self-renewal and phenotypic differentiation into all types of neural cells, has the potential for supplying different cell types under controlled conditions. Second, the use of collagen, which is the most widespread ECM protein in mammalian tissues, provides a scaffold for cell growth in three-dimensions. The matrix is useful for the growth of anchorage-dependent cells like neural stem and progenitor cells into neuronal circuits and networks. Third, RWV bioreactors provide simulated microgravity that creates low fluid shear stress and randomized gravitational vectors. Compared to cultures under static 1 g conditions, the RWV-generated tissues contain cells with significantly higher rates of proliferation and survival. The majority of cells aggregating into spheres in static cultures died in 4-5 weeks while RWV cultures promoted compact aggregates, which became transformed into a multi-layered tissue without a necrotic core. Thus far, the functional engineered tissue-like constructs can be maintained in vitro for up to 10 weeks. This method demonstrates the promise of utility of tissue-engineered constructs not only for in vitro studies of neural stem cell biology, but also for a tissue replacement strategy with new functional brain-like tissues.

The novel approach described herein would be amenable to build different neural tissue models depending on controlled conditions. For example, a combination of bFGF, epidermal growth factor (EGF), and leukemia inhibitory factor (LIF) would be a potent synergistic stimulation of neural stem cell proliferation that generates a continuously proliferating population of immature cells. In order to generate more excitable neurons and active synaptic activity, an early withdrawal of bFGF and addition of brain derived neurotrophic factor (BDNF) are necessary. Furthermore, the method described herein would be amenable to build other types of tissue models. As shown previously, a cell-polymer-bioreactor system was used to promote chondrogenesis (Freed, 1997) and cardiac tissue formation (Carrier, 1999). This strategy could also be used to generate functional CNS tissue constructs derived from neural stem and progenitor cells from a variety of species including humans. Thus, in the future the in vitro model could be scaled-up for clinical use. In addition, this method can be applied to the generation of a cheap and reproducible in vitro system with greater control of variables for the testing of drugs and for detection of environmental toxins.

Having described the invention, the following example is given to illustrate specific applications of the invention. These specific examples are not intended to limit the scope of the invention described in this application.

Example

Cell-collagen constructs were prepared as described previously (O'Connor, 2000). Briefly, collagen (Rat tail tendon, Type I, Boehringer Mannheim Corp., Indianapolis, Ind.), purchased as a sterile, lyophilized powder, was dissolved to a final concentration of 3 mg/mL by addition of sterile 0.2% v/v acetic acid (pH 3-4). To prepare gels, the collagen solution was diluted with an equal volume of 2× phosphate-buffered saline (PBS, Gibco) and an amount of cell media to achieve a final collagen concentration of 0.5 mg/mL (maintaining physiological osmolarity, 250-300 mOsM). After adjusting the pH of the collagen solution to pH 7.4 by the addition of 1 N NaOH, the solution was chilled in an ice bath to prevent gel formation. Cells were taken from embryonic day 13 rat cortex, in which more than 95% cells are proliferative. Cells were added at the desired density, along with more cell media, if necessary, to obtain a final collagen concentration of 0.4 mg/mL. The cell-collagen solution was allowed to warm at room temperature and after approximately 10 min, 0.4 mL aliquots of the collagen-cell suspension were placed into wells of 24-well tissue culture plates. The gels were placed in an incubator (37° C., 5% $CO_2$, 20% $O_2$, 99% Rh) for 1-2 hr to allow gel formation. Once the gel had set, 0.5 mL of cell media was added to the top of the gels and the matrix was returned to the incubator. Neural progenitor cells were immobilized by preparing a suspension of cells in a pre-gel solution of collagen at a cell density of $2\times10^5$/mL.

Figure 2:
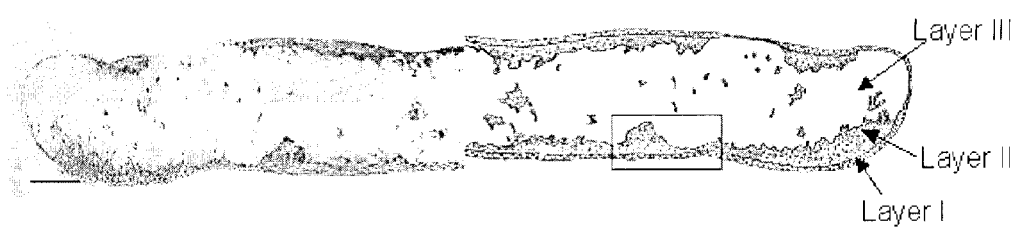
FIG. 2 shows H & E staining of the construct and its drawing.
Figure 3:
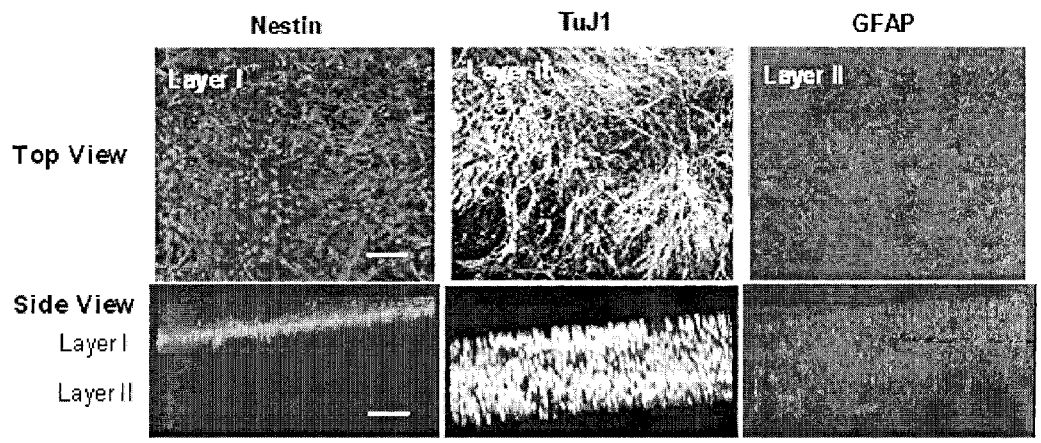
FIGS. 3 and 4 show immunostaining of the intact construct (FIG. 3) and its transverse sections (FIG. 4).
Figure 4:
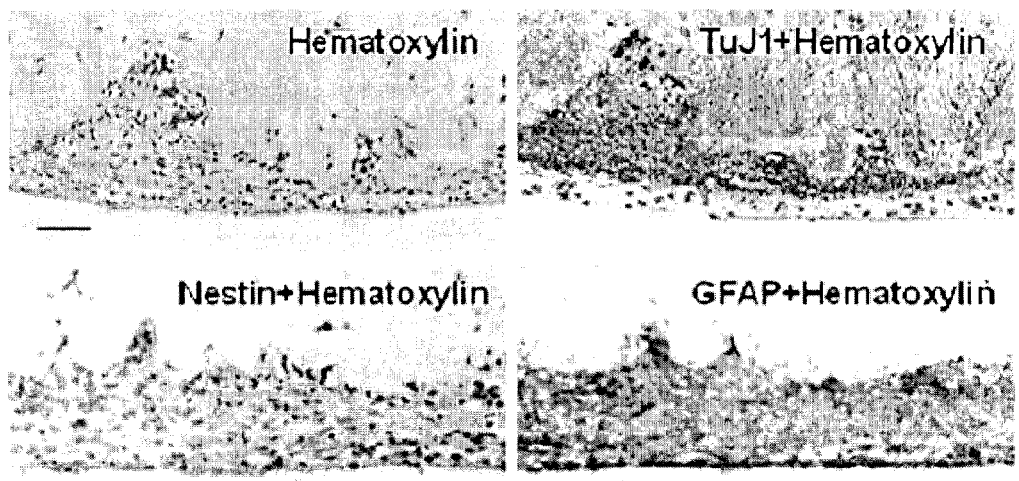
Figure 5:
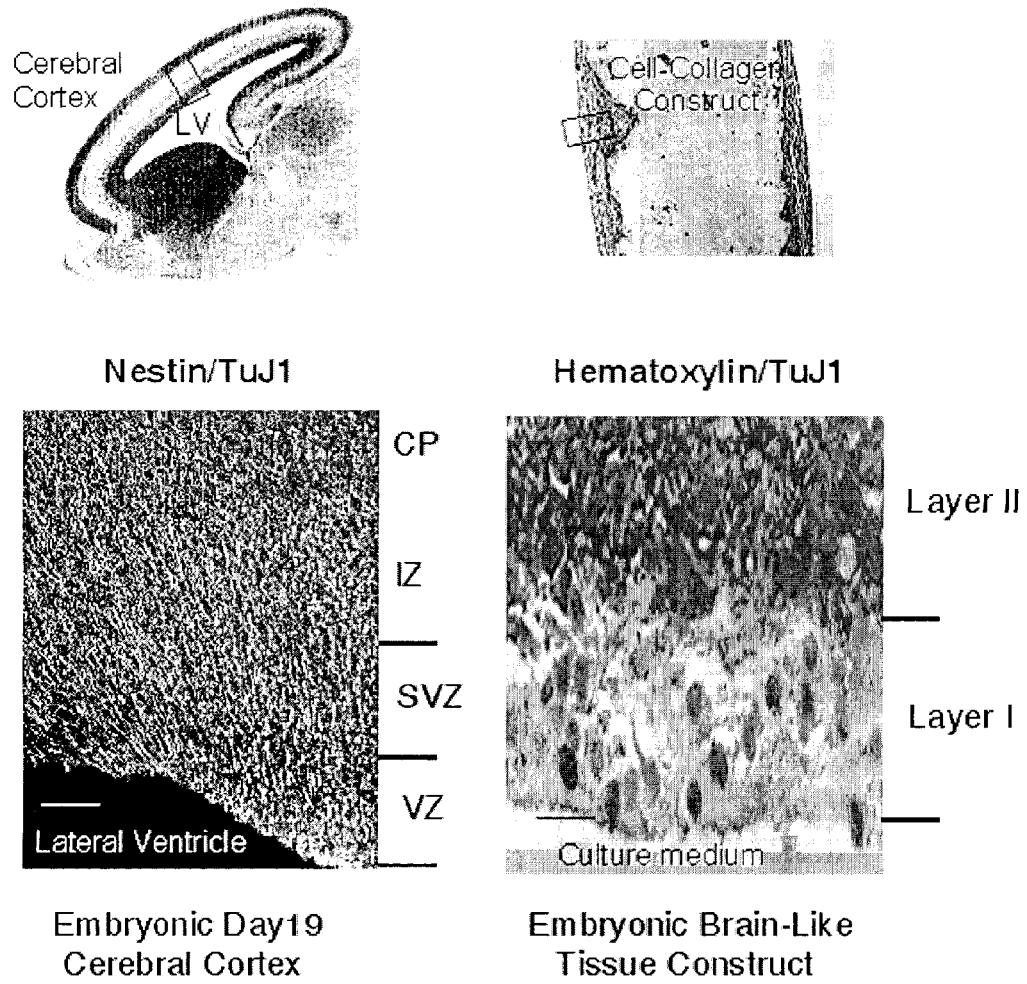
FIG. 5 shows the similarity between a developing rat cerebral cortex and a RWV-generated embryonic brain-like tissue construct.

The primary neural stem and progenitor cells were cultured in the cell-collagen-bioreactor system for up to 10 weeks in a serum-free medium containing bFGF and together with BDNF. The collagen-entrapped neural stem and progenitor cells actively proliferated and differentiated into the major neural phenotypes composing the central nervous system, including neurons, astrocytes, and oligodendrocytes. The cell-collagen constructs cultured in RWV bioreactors gradually compacted 3-4 fold and became elliptically shaped, tissue-like structures (FIGS. 1 and 2) averaging 5 mm in diameter. The compact size of the tissue contrasts with the progressive expansion of neuroepithelial cells, which were cultured under static conditions (without rotation). Cells grown in the latter environment expanded faster but many of the cells do not survive after 4 weeks. Inspection of the tissue-like structure consistently revealed multiple layers of cells, which were populated by different phenotypes. Immunostaining of the intact construct (FIG. 3) or transverse sections through the construct (FIG. 4) revealed the different phenotypes and their distributions. The external layer composing the surface of the tissue (layer I, interfacing with the culture medium) consisted of a thin sheet of progenitor cells (nestin$^+$, vimentin$^+$ and PCNA$^+$; FIGS. 3 and 4). The deeper layer (layer II) was composed of a thicker uneven and continuous mass of differentiating neurons (TuJ1$^+$; FIG. 1Ab and B), astrocytes (GFAP$^+$; FIGS. 3 and 4), and oligodendrocytes (O4$^+$; not shown). In the center core (layer III) there were small, scattered aggregates of neurons (TuJ1$^+$) and glial (GFAP$^+$ or O4$^+$) cells distributed throughout the collagen matrix. The multiple layers of different phenotypes composing the RWV-generated tissue are reminiscent of the developing rat cerebral cortex (FIG. 5). Proliferating neural stem and progenitor cells form the ventricular zone/subventricular zone (VZ/SVZ) while differentiating neuronal and glial phenotypes were found in the cortical plate/subplate (CP/SP) regions. Thus, the outside of the tissue (layer I) corresponds to the VZ/SVZ, while the layer II emulates the CP/SP regions. Layer III may be similar to the intermediate zone (IZ), which is relatively cell poor. However, in the primary tissue the IZ lies between the VZ/SVZ and the CP/SP. The growth conditions imposed here may have displaced this aspect of normal architecture. Alternatively, layer III is composed of differentiating phenotypes that have migrated away from layer II. In this case, the developing tissue is compacted by the rotational forces so that although the tissue is polarized into a neuroepithelial sheet of neural progenitor cells (layer I) and a multi-layer region of differentiating phenotypes (layer II), it is missing the intermediate zone. Finally, progenitor cells in layer I and some cells in layer II showed an ability to synthesize fibronectin (not shown), a unique ECM protein in the CNS.

Figure 6:
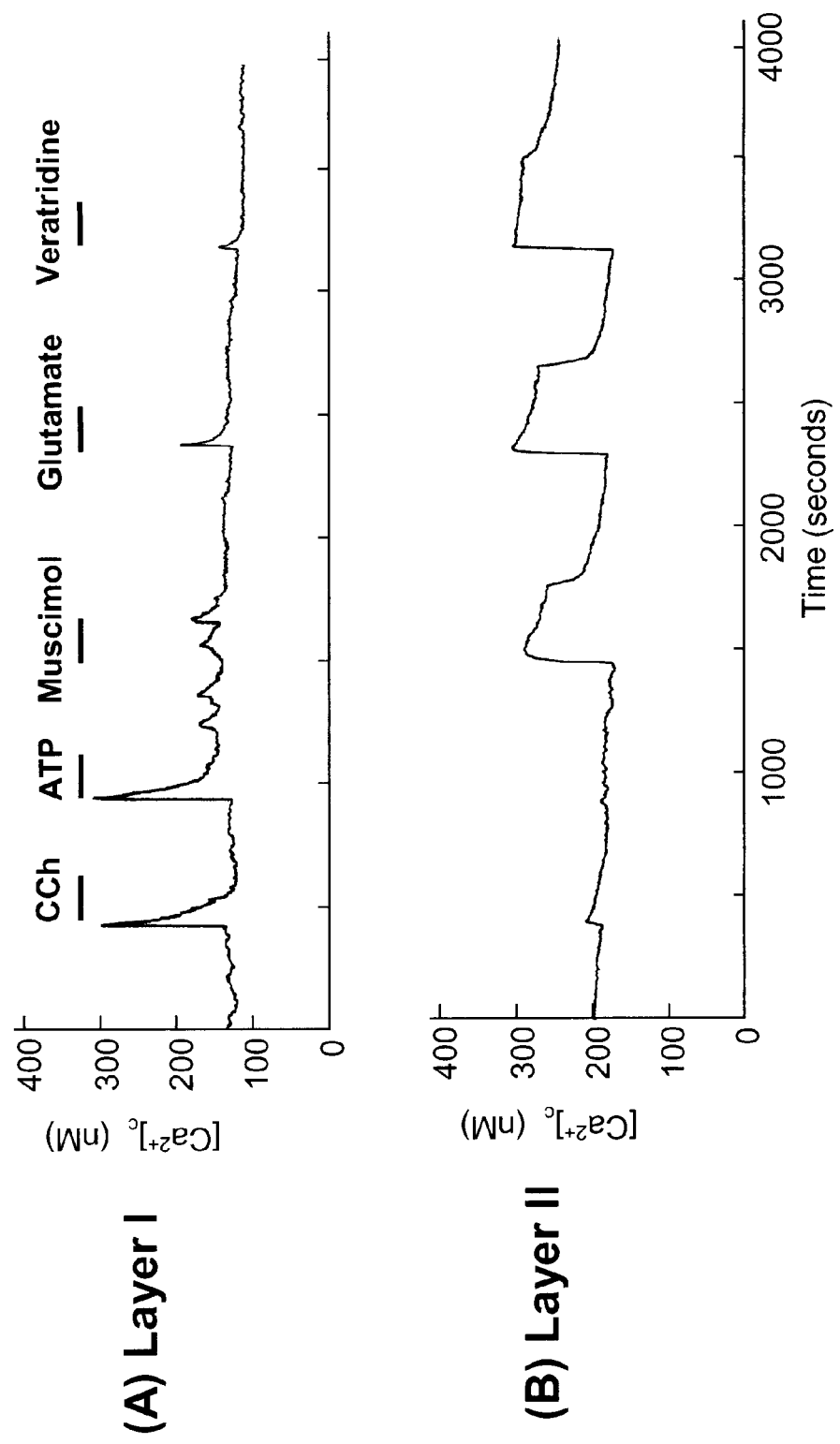
FIG. 6 shows the activation of neurotransmitter receptors in the construct.

The distributions of functional receptors for neurotransmitters and $Na^+$ channels among cells composing layers I and II was investigated using $Ca^{2+}$ imaging. The layers were carefully separated before the cells were loaded with $Ca^{2+}$ indicator dye. Sequential exposure to agonists at four major neurotransmitter receptors (cholinergic, purinergic, GABAergic and glutamatergic) revealed that the vast majority of cells (86%) in layer I responded to ATP, which activates purinergic receptors (FIG. 6, CCh activates mAChRs, ATP activates purinergic receptors, muscimol activates $GABA_A$ receptors, glutamate is an excitatory transmitter, and veratridine activates $Na^+$ channels.). The rise in cytosolic $Ca^{2+}$ ($Ca^{2+}$ c) was high in amplitude and transient, relaxing to the baseline during the exposure. About half (55%) the cells responded to carbarchol, an agonist at muscarinic cholinergic receptors with a lower amplitude $Ca^{2+}$c response, which was also transient. Few cells responded to the other agonists and all of these latter cells were clustered together. In contrast, few cells in layer II responded to ATP and those that did not exhibited low amplitude responses. The majority of cells responded to each of the other agonists. These differential results on cells in layers I and II parallel previously published results on proliferating precursor cells in the VZ/SVZ and differentiating neurons in the CP/SP (Maric, 2003). Thus, the two cell layers composing the engineered tissue exhibit properties similar to those developing in vivo.

Figure 7:
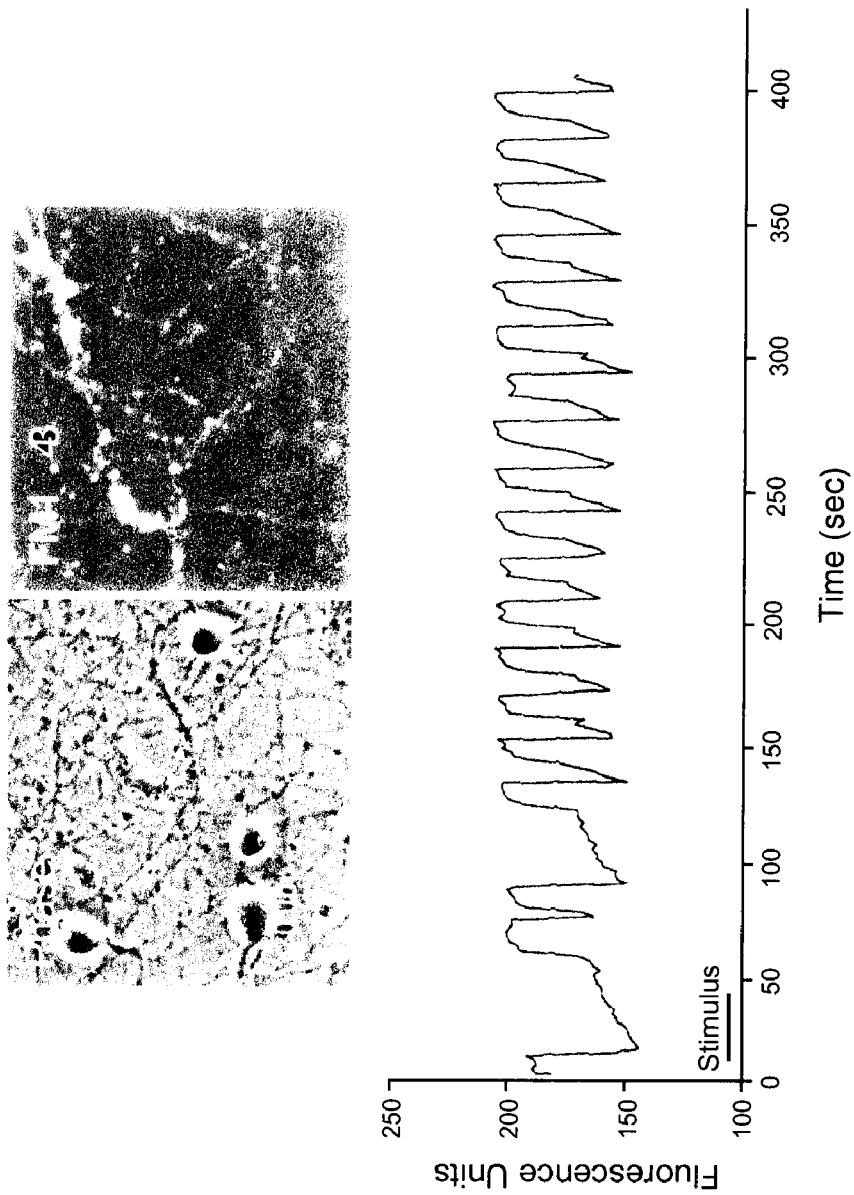
FIG. 7 shows actived synaptic vesicle recycling in the construct upon $K^+$ stimulation.

The second functional assay using an endocytotic marker (FM43-1) showed that cells in layer II, but not those in layer I, were stained with FM1-43, which has been used to label recycling synaptic vesicles in neuronal networks. FM1-43 fluorescence intensity was reduced upon $K^+$ stimulation (FIG. 7), demonstrating synaptic vesicle recycling at active neuronal circuits.

Obviously, many modifications and variations of the present invention are possible in light of the above teachings. It is therefore to be understood that the claimed invention may be practiced otherwise than as specifically described.

REFERENCES

All references are incorporated herein by reference.

Bellamkonda et al., 1998. Hydrogel-based three-dimensional matrix for neural cells. *J. Biomed. Mater. Res.*, 29, 663-671.

Carrier et al., 1999. Cardiac tissue engineering cell seeding, cultivation parameters, and tissue construct characterization. *Biotechol Bioeng.*, 64:580-589

Fisher, 1997. Neural precursor cells: Applications for the study and repair of the central nervous system. *Neurobiology of Disease*, 4, 1-22.

Freed et al., 1997. Tissue engineering of cartilage in space. *Proc. Nat. Acad. Sci. USA*, 94:13885-13890

Freed et al., 1995. Cultivation of Cell-Polymer Tissue Constructs in Simulated Microgravity. *Biotech. and Bioeng.* 46, 306-313.

Gage, 1998. Stem cells of the central nervous system. *Current Opinion in Neurobiology* 8, 671-676.

Gage, 2000. Mammalian neural stem cells. *Science* 287, 1433-1438.

Gage et al., 1995. Survival and differentiation of adult neuronal progenitor cells transplanted to the adult brain. *Proc. Natl. Acad. Sci. USA* 92, 11879-11883.

Goodwin et al., 1993. Rotating wall vessel coculture of small intestine as a prelude to tissue modeling: Aspects of simulated microgravity. *Proc. Soc. Exp. Biol. Med.* 202:181-192

Jessup et al., 1993. Prospects for use of microgravity-based bioreactors to study three-dimensional host-tumor interactions in human neoplasia. *J Cell Bioch.* 51:290-300.

Low et al., 2001. Neural precursor cells form rudimentary tissue-like structures in a rotating-wall vessel bioreactor. *In Vitro Cell: Dev. Biol.-Animal* 37, 141-147.

Ma et al., CNS stem and progenitor cell differentiation into functional neuronal circuits in three-dimensional collagen gels. *Exp. Neurology* in press, 2004

Ma et al., 1998. Basic FGF-responsive telencephalic precursor cells express functional $GABA_A$ receptor/$Cl^-$ channels in vitro. *J. Neurobiol.* 35, 277-286.

Ma et al., 2000. Acetylcholine stimulates cortical precursor cell proliferation via muscarinic receptor activation and MAP kinase phosphorylation. *Eur. J. Neurosci.* 12, 1227-1240.

Maric et al., 2000. Functional ionotrophic glutamate receptors emerge during terminal cell division and early neuronal differentiation of rat neuroepithelial cells. *J. Neurosci. Res.* 61, 652-662.

Maric et al., 2003. Prospective cell sorting of embryonic rat neural stem cells and neuronal and glial progenitors reveals selective effects of basic fibroblast growth factor and epidermal growth factor on self-renewal and differentiation. *J. Neurosci.* 23, 240-251.

Margolis et al., 1999. Long term organ culture of human prostate tissue in a NASA-designed rotating wall bioreactor. *J Urology* 161-290

McKay, 1997. Stem cells in the CNS. *Science* 276, 66-71.

O'Connor et al., 2000. Primary neural precursor cell expansion, differentiation and cytosolic $Ca^{2+}$ response in three-dimensional collagen gel. *J. Neurosci. Methods* 102, 187-195.

O'Connor et al., 2001. Survival and neurite outgrowth of rat cortical neurons in three-dimensional agarose and collagen gel matrices. *Neuroscience letter* 304:189-193.

O'Shaughnessy et al., 2003. Functional synapse formation among rat cortical neurons grown on three-dimensional collagen gels. *Neurosci. Let.* 340, 169-72.

Ruoslahti, 1997. Stretching is good for a cell. *Science.* 276, 1345-6.

Unsworth et al., 2000. Tissue assembly in microgravity. In Principles of Tissue Engineering, Eds. by Lanza, Langer and Vacanti, pp 157-164, Academic Press, San Diego.

Woerly et al., 1999. Neural tissue formation within porous hydrogels implanted in brain and spinal cord lesions: ultrastructural, immunohistochemical, and diffusion studies. *Tissue Eng.* 5, 469-488.

What is claimed is:

1. A method comprising the steps of:
providing primary mammalian neural stem cells and progenitor cells;
placing the stem cells and the progenitor cells in an extracellular matrix; and
maintaining the matrix in a culture medium and a microgravity environment;
wherein the microgravity environment is created in a bioreactor rotating vertically at 10-15 RPM.

2. The method of claim 1;
wherein the extracellular matrix comprises type I collagen; and
wherein the culture medium comprises basic fibroblast growth factor and brain derived neurotrophic factor.

3. The method of claim 2, wherein the neural stem cells and progenitor cells are rat cells.

4. The method of claim 3, wherein the method produces tissue.

5. The method of claim 2, wherein the neural stem cells and progenitor cells are human cells.

6. The method of claim 5, wherein the method produces tissue.

* * * * *